United States Patent [19]

Totani et al.

[11] Patent Number: 4,577,038

[45] Date of Patent: Mar. 18, 1986

[54] GLYCOLIC ACID TYPE PLATINUM COMPLEXES

[75] Inventors: Tetsushi Totani, Hyogo; Katsutoshi Aono, Nara, both of Japan

[73] Assignee: Shionogi & Co., Ltd., Osaka, Japan

[21] Appl. No.: 606,961

[22] Filed: May 4, 1984

[30] Foreign Application Priority Data

Jun. 1, 1983 [JP] Japan ................................. 58-98631

[51] Int. Cl.[4] ............................................. C07F 15/00
[52] U.S. Cl. .................................................. 556/137
[58] Field of Search .................... 260/429 R; 424/287; 556/137; 514/492

[56] References Cited

U.S. PATENT DOCUMENTS

| | | | |
|---|---|---|---|
| 4,225,529 | 9/1980 | Hydes et al. | 260/429 R |
| 4,230,631 | 10/1980 | Hydes et al. | 260/429 R |
| 4,250,189 | 2/1981 | Hydes et al. | 260/429 R X |
| 4,271,085 | 6/1981 | Amundsen et al. | 260/429 R |
| 4,359,425 | 11/1982 | Totani et al. | 260/429 R |
| 4,466,924 | 8/1984 | Verbeek et al. | 260/429 R |

OTHER PUBLICATIONS

Chemical Abstracts 92 51723v (1980), 92 88521d (1980).
Chemical Abstracts 93 125662u (1980), 93 125663v (1980).
Chemical Abstracts 78 105899p (1973).
Chemical Abstracts 80 66593d (1973).

*Primary Examiner*—Helen M. S. Sneed
*Attorney, Agent, or Firm*—Wenderoth, Lind & Ponack

[57] ABSTRACT

Novel platinum complexes of glycolic acid type having potent antitumor activity and high water solubility with low nephrotoxicity and a pharmaceutical composition containing one or more said compounds together with one or more carriers, diluents or excipients are provided. They can be administered parenterally to patients suffering from malignant tumors.

They are prepared by passing nitrato-platinum complexes of amines through anion exchange resins and subsequent reaction with glycolic acids.

14 Claims, No Drawings

GLYCOLIC ACID TYPE PLATINUM COMPLEXES

BACKGROUND OF THE INVENTION

1. Field of the Invention

The present invention relates to novel platinum complexes of glycolic acid type which have antitumor activity comparable to or more potent than that of cisplatin. The nephrotoxicity is very low and the water solubility is high.

2. Description of the Prior Art

Compounds analogous to cisplatin [U.S. Pat. Nos. 3,892,790 and 3,904,663] have intensively been investigated since its potent antitumor activity was observed; as the result of the fact, compounds such as malonato(1,2-diaminocyclohexane)platinum(II) [U.S. Pat. No. 4,169,846], sulfato(1,2-diaminocyclohexane)platinum-(II) [U.S. Pat. Nos. 4,200,583 and 4,256,652], 4-carboxyphthalato(1,2-diaminocyclohexane)platinum(II) [British Patent Publication No. 2,003,468], cis-dichloro-trans-dihydroxy-bis(isopropylamine)platinum(IV) [U.S. Pat. No. 4,394,319], and the like are known presently.

The present inventors have also been studying compounds analogous to cisplatin and prepared various new types of platinum complexes having potent antitumor activity and high water solubility, for example, novel platinum complexes [British Patent Publication No. 2,091,731], and the like.

BRIEF SUMMARY OF THE INVENTION

The present invention relates to novel platinum complexes of glycolic acid type. More particularly, it relates to the compounds of the formula (I) and a pharmaceutical composition comprising one or more said compounds as effective ingredients.

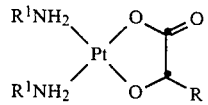

(wherein R is $C_1$–$C_6$ alkyl, hydroxymethyl, halomethyl, or phenyl; $R^1$ is hydrogen or $C_1$–$C_6$ alkyl; with proviso that R is not hydroxymethyl, when $R^1$ is hydrogen).

The compounds (I) are prepared according to the following reaction sequence.

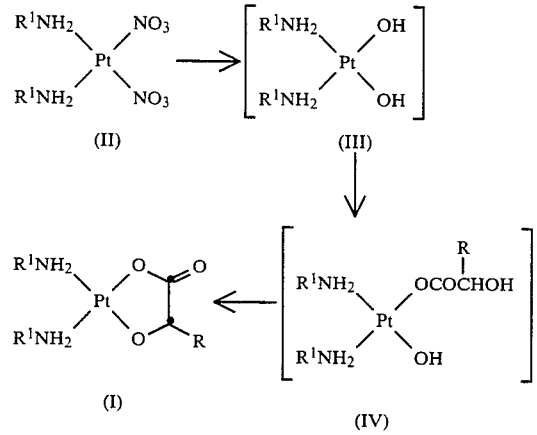

(wherein R and $R^1$ each has the same significance as defined above).

The compounds (I) are useful as parenterally administrable antitumor agents with low nephrotoxicity.

DETAILED DESCRIPTION OF THE INVENTION

The present invention relates to novel platinum complexes of glycolic acid type. More particularly, it relates to the compounds of the formula (I) and a pharmaceutical composition comprising one or more said compounds as effective ingredients.

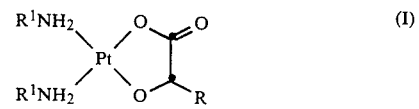

(wherein R is $C_1$–$C_6$ alkyl, hydroxymethyl, halomethyl, or phenyl; $R^1$ is hydrogen or $C_1$–$C_6$ alkyl; with proviso that R is not hydroxymethyl, when $R^1$ is hydrogen).

The meanings of the terms used in the above definition are shown below:

the $C_1$–$C_6$ alkyl includes methyl, ethyl, n-propyl, isopropyl, n-butyl, isobutyl, tert-butyl, n-pentyl, isopentyl, sec-pentyl, neo-pentyl, n-hexyl, sec-hexyl, and the like; the halomethyl means methyl to which 1 to 3 halogen atoms such as fluorine, chlorine, bromine, iodine, and the like are bound, for example, monochloromethyl, dichloromethyl, monofluoromethyl, trifluoromethyl, monobromomethyl, monoiodomethyl, and the like.

The compounds (I) of the present invention can easily be prepared according to the following reaction sequence.

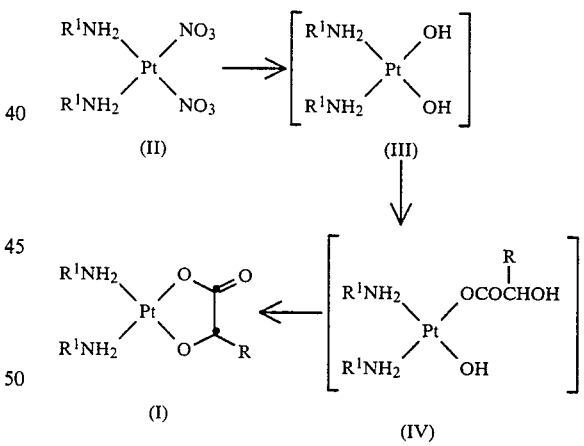

(wherein R and $R^1$ each has the same significance as defined above).

In the reaction sequence described above, an aqueous solution of the compounds (II) is passed through a column of anion exchange resin ($OH^-$ type) such as Amberlite IRA-400 (Rohm & Haas Co.), Dowex I (Dow Chemical Co.), or Daiaion SA-10A (Mitsubishi Chemical Industries Ltd.) to give an aqueous solution containing the compounds (III) as main product in which the two nitrato groups are replaced by hydroxy groups. Preferably, the resulting compounds (III) are usually used as the solution separated above in the next step since these compounds are unstable in solid form.

An aqueous solution of the compounds (III) is allowed to react with glycolic acid to give the desired compounds (I) of the present invention, probably through the intermediate compounds (IV). The reaction of the compounds (II) to produce the compounds (III) proceeds quantitatively, so glycolic acid may be used in an equivalent amount to the compounds (II). The present reaction is usually carried out at room temperature and terminates within 10 days; if necessary the reaction may be conducted at an elevated temperature of, for example, 50°–70° C.

The starting compounds (II) described in the above, reaction sequence are known, or may be obtained by the reaction of the known compounds of the formula:

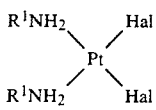

(wherein $R^1$ has the same significance as defined above; Hal is halogen, e.g. chlorine, bromine, or iodine) with silver nitrate.

The compounds of the present invention may take polymeric forms, for example, a dimer structure as shown below.

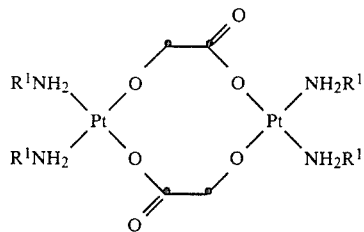

(wherein $R^1$ has the same significance as defined above).

The compounds of the present invention have the antitumor activity comparable to or more potent than that of cisplatin with lower neophrotoxicity. Furthermore, they can easily be administered parenterally to patients suffering from malignant tumors since they are highly soluble in water. Thus, for example, the compounds (I) may be dissolved or suspended in appropriate solvents for injection (e.g., distilled water for injection, physiological saline, 5% glucose aqueous solution, 5% mannitol aqueous solution, aqueous ethanol, aqueous glycerin, and aqueous propylene glycol), and can be administered intravenously, intramuscularly, or subcutaneously, or by means of instillation. The compounds (I) may be placed in sealed ampoules as solutions or suspensions, or more preferably preserved in ampoules or vials in solid forms, e.g., crystals, powders, fine crystals, or lyophilizates suitable to be dissolved immediately before used. Stabilizers may also be added.

The present invention includes a pharmaceutical or veterinary formulation comprising a compound of the present invention. Such formulations may contain one or more usual carriers, diluents, or excipients.

The Examples of compounds of the present invention are:
(Lactato-O,O')-cis-diammineplatinum(II),
(L-Lactato-O,O')-cis-diammineplatinum(II),
(β-Chlorolactato-O,O')-cis-diammineplatinum(II),
(Mandelato-O,O')-cis-diammineplatinum(II),
(β-Chlorolactato-O,O')-cis-bis(methylamine)platinum-(II),
(Glycerato-O,O')-cis-bis(methylamine)platinum(II), (2-Ethylglycolato-O,O')-dis-diammineplatinum(II),
(2-Iso-butylglycolato-O,O')-cis-diammineplatinum(II), and
(2-n-Hexylglycolate-O,O')-cis-diammineplatinum(II).

The present invention will be explained in more detail by the following Examples and Experiment.

EXAMPLE 1(a)

(Lactato-O,O')-cis-diammineplatinum(II) 3a

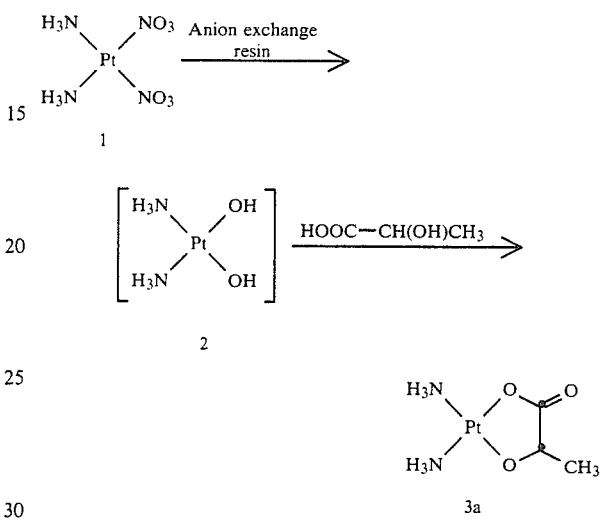

Cis-dinitrato-cis-diammineplatinum(II) 1 (1.5 g, 4.25 mmol) is dissolved in 30 ml of water with heating, and the mixture is cooled and passed through a column of 30 ml of an anion exchange resin Daiaion SA 10A (OH$^-$ type). To the eluate is dropwise added 54 ml of an aqueous solution of lactic acid (4.25 mmol) with stirring. The mixture is allowed to stand overnight, concentrated to 15 ml, and heated at 65° C. for 3 hours. The reaction mixture is purified by passing through a column of silica-gel to give 0.63 g (yield: 45%) of the objective compound 3a. m.p. higher than 155° C. (decomp.).

Anal. Calcd. (%) [for $C_3H_{10}N_2O_3Pt(H_2O)_{0.5}$]: C, 11.05; H, 3.40; N, 8.58; Pt, 59.80. Found (%): C, 11.06; H, 3.38; N, 8.65; Pt, 60.08.

IR; $\nu_{max}^{Nujol}$ 3300–3100 (broad, s), 1605 (s) cm$^{-1}$.

EXAMPLE 1(b)

(L-Lactato-O,O')-cis-diammineplatinum(II) 3b

The compound 1 (4.5 g, 12.75 mmol) is dissolved in 90 ml of water with heating, and the solution is cooled and passed through a column of 90 ml of an anion exchange resin Daiaion SA 10A (OH$^-$ type). To the eluate is added 1.15 g (12.75 mmol) of crystalline L-lactic acid in small portions with stirring. The reaction mixture is allowed to react with heating in the same manner as in Example 1(a), and purified by passing through a column of silica-gel. The resulting solid is further recrystallized from methanol. The crystals are once dissolved in a small amount of water to remove the recrystallization solvent (methanol) and the solution evaporated to dryness at 60° C. under reduced pressure. The yield of 3b is 1.6 g (37%). m.p. higher than 155° C. (decomp.).

Anal. Calcd. (%) [for $C_3H_{10}N_2O_3Pt(H_2O)_{0.5}$]: C, 11.05; H, 3.40; N, 8.58; Pt, 59.80. Found (%): C, 11.01; H, 3.30; N, 8.62; Pt, 59.52.

IR; $\nu_{max}^{Nujol}$ 1580(sh), 1315(m), 1295(m), 1115(m), 1090(w), 1045(m), 925(w), 870(m), 770(w), 720(w) cm$^{-1}$.

$^1$HNMR: (in D$_2$O, ppm from TMS as the external standard, δ) 1.75 (doublet, 3H, —CH$_3$), 4.60 (octet, 1H, $J_{195\text{-}H}$=28 Hz).

EXAMPLE 2

(β-Chlorolactato-O,O')-cis-diammineplatinum(II) 4

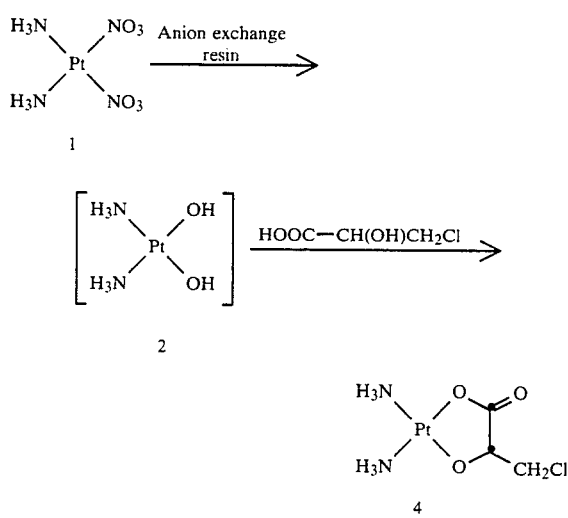

The compound 1 (1.5 g, 4.25 mmol) is dissolved in 30 ml of water with heating, and the solution is cooled and passed through a column of 30 ml of an anion exchange resin Daiaion SA 10A (OH$^-$ type). To the eluate is dropwise added a solution of 529 mg (4.25 mmol) of β-chlorolactic acid in 5 ml of water with stirring. The mixture is allowed to stand overnight, concentrated to 13 ml, and heated at a temperature of 45°-55° C. for 5 hours. The reaction mixture is concentrated under reduced pressure, and the precipitating gray solid is collected and purified by chromatography on a column of silica-gel. The eluate is recrystallized from water to give 0.67 g (43%) of the objective compound 4. m.p. 145° C. (decomp.).

Anal. Calcd. (%) [for C$_3$H$_9$N$_2$O$_3$ClPt(H$_2$O)$_{1.0}$]: C, 9.77; H, 3.01; N, 7.60; Cl, 9.34; Pt, 52.92. Found (%): C, 9.24; H, 2.85; N, 7.58; Cl, 9.49; Pt, 53.09.

IR; $\nu_{max}^{Nujol}$ 3480(m), 3340(sh), 3085(m), 1590(s), 1420(m), 1350(w), 1325(m), 1285(m), 1265(w), 1195(w), 1080(s), 910(m), 875(m), 830(m), 770(w) cm$^{-1}$.

$^1$HNMR: (in D$_2$O, ppm from TMS as the external standard, δ) 4.12 (doublet 2H, —CH$_2$—), 4.83

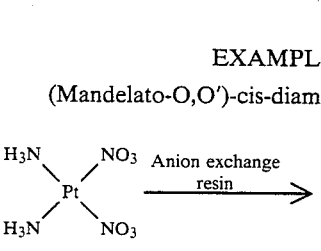

EXAMPLE 3

(Mandelato-O,O')-cis-diammineplatinum(II) 5

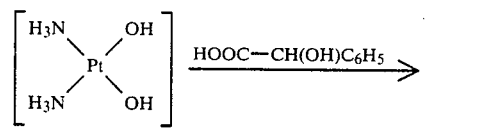

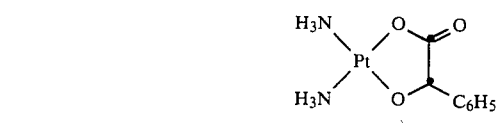

Mandelic acid (365 mg, 2.4 mmol) is added to 50 ml of an aqueous solution of the compound 2 (2.5 mmol) provided from the compound 1 using an anion exchange resin in the same manner as in Example 1, and the mixture is allowed to react at 55° C. for 4 hours. The reaction mixture is concentrated, and the residual solid is dissolved in methanol, and the mixture is purified by passing through a column of silica-gel, and finally recrystallized from methanol to give 0.45 g (48%) of the objective compound 5 as light yellow crystals. m.p. higher than 185° C. (decomp.).

Anal. Calcd. (%) [for C$_8$H$_{12}$N$_2$O$_3$Pt]: C, 25.33; H, 3.19; N, 7.38; Pt, 51.43. Found (%): C, 24.58; H, 3.26; N, 7.36; Pt, 51.87.

IR; $\nu_{max}^{Nujol}$ 3250(m), 3050(m), 1630(s), 1590(m), 1570(m), 1330(s), 1240(m), 1180(w), 1040(m), 940(w), 840(w), 830(w), 750(w) cm$^{-1}$.

$^1$HNMR: (in D$_2$O, ppm from TMS as the external standard, δ) 3.5–5.0 (broad, NH$_3$), 5.30

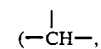

$J_{195Pt\text{-}H}$=36 Hz), 7.8–8.2 (multiplet C$_6$H$_5$).

EXAMPLE 4

(β-Chlorolactato-O,O')-cis-bis(methylamine)platinum-(II) 8

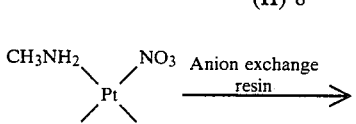

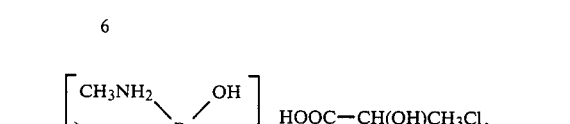

β-Chlorolactic acid (90 mg, 0.73 mmol) is added to 30 ml of an aqueous solution of the compound 7 (0.75 mmol) provided from cis-dinitrato-cis-bis(methylamine)platinum(II) 6 using an anion exchange resin in the same manner as in Example 1, and the mixture is allowed to react at 55° C. for 4 hours. The reaction mixture is evaporated to dryness, dissolved in methanol, and purified by passing through a column of silica-gel. The product is recrystallized from methanol-acetone to give 0.1 g (35%) of the objective compound 8 as colorless highly hygroscopic crystals.

Anal. Calcd. (%) [for $C_5H_{13}N_2O_3ClPt$]: C, 15.82; H, 3.45; N, 7.38; Cl, 9.34; Pt, 51.38. Found (%): C, 15.74; H, 3.76; N, 6.99; Cl, 9.48; Pt, 50.54.

IR; $\nu_{max}^{Nujol}$ 3250(m), 3150(s), 1600(sh), 1580(s), 1410(s), 1290(w), 1190(w), 1090(s), 1000(w), 910(w), 870(w), 825(w), 720(w) cm$^{-1}$.

$^1$HNMR: (in $D_2O$, ppm from TMS as the external standard, δ) 1.83, 1.90 (singlet with satellite signals, methylamine $CH_3$—), 3.18–3.22 (β-chlorolactato

3.89 (β-chlorlactato

3.5–4.5 (methylamine $NH_2$).

EXAMPLE 5

(Glycerato-O,O')-cis-bis(methylamine)platinum(II) 9

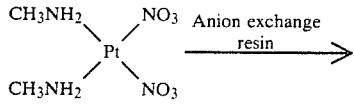

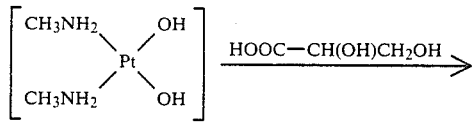

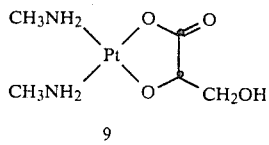

Glyceric acid (0.24 g, 2.3 mmol) is added to 60 ml of an aqueous solution of the compound 7 (2.4 mmol) provided from the compound 6 using an anion exchange resin in the same manner as in Example 1, and the mixture is allowed to stand at room temperature overnight and then at 55° C. for 6 hours. The reaction mixture is evaporated to dryness, dissolved in methanol, and purified by passing through a column of silica-gel. The product is recrystallized from methanol-acetone to give 0.46 g (53%) of the objective compound 9 as colorless highly hygroscopic crystals.

Anal. Calcd. (%) [for $C_5H_{14}N_2O_4Pt(CH_3COCH_3)_{0.2}$]: C, 18.04; H, 4.10; N, 7.51; Pt, 52.31. Found (%): C, 17.68; H, 3.96; N, 7.38; Pt, 52.11.

IR; $\nu_{max}^{Nujol}$ 3350(w), 3200(m), 3120(m), 1620(s), 1300(w), 1090(m), 1030(w), 1000(w), 880(w), 830(w), 710(w) cm$^{-1}$.

$^1$HNMR: (in $D_2O$, ppm from TMS as the external standard, δ) 1.85, 1.87 (methylamine $CH_3$—), 3.17 (glycerato —$CH_2$—), 3.55 (glycerato

3.5–4.5 (broad, $NH_2$).

EXAMPLE 6

(2-Ethylglycolato-O,O')-cis-diammineplatinum(II) 10

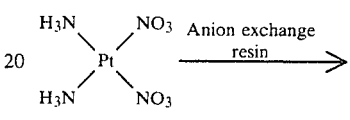

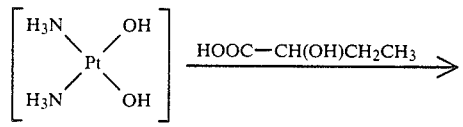

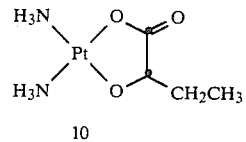

The compound 1 (3 g, 8.5 mmol) is dissolved in 90 ml of water with heating, and the solution is cooled and passed through a column of 60 ml of an anion exchange resin Daiaion SA 10A (OH$^-$ type). To the eluate is added 885 mg (8.5 mmol) of α-hydroxybutyric acid, and the mixture is dissolved with stirring. The mixture is allowed to stand overnight, heated at 68° C. for 4 hours, and then concentrated. The residue is purified by chromatography with silica-gel (developer: water-ethanol (1:5)), and the fractions of which Rf values 0.41 are collected to give 860 mg (28%) of the objective compound 10. m.p. 180°–185° C. (decomp.).

Anal. Calcd. (%) [for $C_4H_{12}N_2O_3Pt(H_2O)_{0.5}$]: C, 14.12; H, 3.85; N, 8.23; Pt, 57.34. Found (%): C, 14.28; H, 3.69; N, 8.26; Pt, 57.67.

IR; $\nu_{max}^{Nujol}$ ~3400(w), ~3150(broad, s), 1610(s), 1360(sh), 1330(sh), 1300(sh), 1270(sh), 1245(sh), 1120(m), 1080(m), 1055(m), 980(m), 930(w), 880(w), 855(w), 825(m), 720(w) cm$^{-1}$.

$^1$HNMR: (in $D_2O$, ppm from TMS as the external standard, δ) 1.47 (t, 7 Hz, 3H, —$CH_3$), 2.07 (m, 2H, —$CH_2$—), 4.53 (t, 5 Hz, 1H, satellite, $J_{195-H}$=31 Hz,

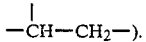

EXAMPLE 7

(2-Iso-butylglycolate-O,O')-cis-diammineplatinum(II) 11

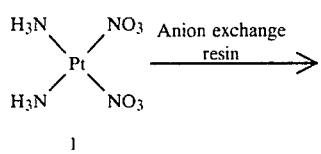

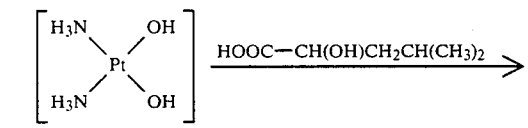

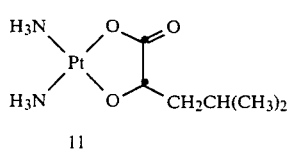

Leucic acid (1.05 g, 8 mmol) is added to 125 ml of an aqueous solution of the compound 2 (8 mmol) provided from the compound 1 by passing through an anion exchange resin in the same manner as in Example 1, and dissolved. The solution is allowed to stand overnight, heated at an elevated temperature of 55°–58° C. for 8 hours, and then concentrated under reduced pressure. The residue is purified by chromatography with silica-gel (developer: water-ethanol (1:5)) and recrystallized from water-ethanol. The crystals are dried in vacuum at 70° C. to give 700 mg (24%) of the objective compound 11. m.p. 175°–185° C. (turn dark with decomposition).

Anal. Calcd. (%) [for $C_6H_{16}N_2O_3Pt$]: C, 20.05; H, 4.49; N, 7.80; Pt, 54.30. Found (%): C, 19.43; H, 4.49; N, 7.80; Pt, 54.35.

IR; $\nu_{max}^{Nujol}$ 3300–3100 (broad), 1620(s), 1350(sh), 1330(sh), 1175(w), 1135(w), 1085(m), 940(m), 840(w), 790(w), 725(w) cm$^{-1}$.

$^1$HNMR: (in $D_2O$, ppm from TMS as the external standard, δ) 1.43 (doublet, 6H, —CH(CH$_3$)$_2$), 2.7–1.8 (multiplet, 3H, —CH$_2$—), 5.1–4.2 (quartet like, satellite coupled with $^{195}$Pt, 1H,

EXAMPLE 8

(2-n-Hexylglycolate-O,O')-cis-diammineplatinum(II)

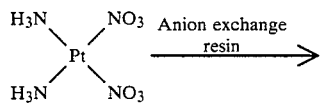

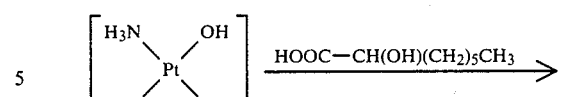

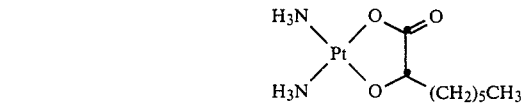

The compound 1 (3 g, 8.5 mmol) is dissolved in 60 ml of water with heating, and the mixture is cooled and treated with 60 ml of an anion exchange resin Daiaion SA 10A (OH$^-$ type). To the eluate is added 1.34 g (8.4 mmol) of α-hydroxy-n-caprylic acid and stirred. The insoluble material is removed by filtration, and the resulting solution is allowed to stand overnight and heated at 60° C. for 7 hours. The mixture is concentrated under reduced pressure and purified by chromatography with silica-gel (developer: water-ethanol (1:10)) to give 1 g (30%) of the objective compound 12. m.p. 160°–175° C. (turn dark with decomposition).

Anal. Calcd. (%) [for $C_8H_{20}N_2O_3Pt(H_2O)_{0.3}$]: C, 24.47; H, 5.29; N, 7.13; Pt, 49.67. Found (%): C, 24.93; H, 5.17; N, 7.29; Pt, 49.46.

IR; $\nu_{max}^{Nujol}$ 3260(m), 3210(sh), 1620(s), 1595(sh), 1320(s), 1290(sh), 1120(w), 1045(m), 910(w), 855(w), 765(w), 710(w) cm$^{-1}$.

$^1$HNMR: (in $D_2O$, ppm from TMS as the external standard, δ) 2.4–1.2 (multiplet, 13H, hexyl group), 4.58 (triplet like, satellite coupled with $^{195}$Pt, 1H,

Experiment 1

Antitumor activity against P388

Test Method

Mouse Leukemia P388 ascites cells (10$^6$ cells) are intraperitoneally inoculated to BDF$_1$ mice (6 to 10 mice are employed in each test group), and from the next day an each predetermined amount of the test compounds is administered intravenously at tail for 5 days.

Test compounds
(A): (Lactato-O,O')-cis-diammineplatinum(II) 3a
(B): Cisplatin

Evaluation of Effect

From the average survival days (a) in the each test group and those (b) of the untreated control group, the increase of lifespan (ILS) is calculated according to the following formula.

$$ILS\ (\%) = \frac{(a) - (b)}{(b)} \times 100$$

Result

| Dose (mg/kg) | ILS (%) (A) | (B) |
|---|---|---|
| 0 × 5 | — | — |
| 0.2 × 5 |  | 6 |
| 0.4 × 5 |  | 6 |
| 1 × 5 |  | 13 |
| 2 × 5 | −3 | 47 |
| 4 × 5 | −5 | −14 |
| 8 × 5 | 4 |  |
| 16 × 5 | 36 |  |
| 32 × 5 | 88 |  |
| 64 × 5 | −19 |  |

An effect is evaluated from a dosage showing 30% increase of lifespan: $ILS_{30}$, a dosage showing maximum increase of lifespan: $ILS_{MAX}$, and a curative index (CI).

$$CI = \frac{ILS_{MAX}}{ILS_{30}}.$$

The larger the CI value is, the more effective it is.

| Compounds | (A) | (B) |
|---|---|---|
| $ILS_{30}$ | 72 mg/kg | 7 mg/kg |
| $ILS_{MAX}$ | 160 mg/kg | 10 mg/kg |
| CI | 2.2 | 1.4 |

What we claim is:

1. A compound of the formula:

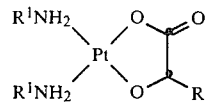

(wherein R is $C_1$–$C_6$ alkyl, hyroxymethyl, halomethyl, or phenyl; $R^1$ is hydrogen or $C_1$–$C_6$ alkyl; with proviso that R is not hydroxymethyl, when $R^1$ is hydrogen).

2. A compound claimed in claim 1, wherein R is methyl, ethyl, iso-butyl, n-hexyl, chloromethyl, phenyl, and $R^1$ is hydrogen or methyl.

3. A compound claimed in claim 1, wherein R is methyl, ethyl, iso-butyl, n-hexyl, chloromethyl, phenyl, and $R^1$ is hydrogen.

4. A compound claimed in claim 1, wherein R is chloromethyl or hydroxymethyl, and $R^1$ is methyl.

5. A compound claimed in claim 1, namely, (lactato-O,O′)-cis-diammineplatinum(II).

6. A compound claimed in claim 1, namely, (L-lactato-O,O′)-cis-diammineplatinum(II).

7. A compound claimed in claim 1, namely, (β-chlorolactato-O,O′)-cis-diammineplatinum(II).

8. A compound claimed in claim 1, namely, (mandelato-O,O′)-cis-diammineplatinum(II).

9. A compound claimed in claim 1, namely, (β-chlorolactato-O,O′)-cis-bis(methylamine)platinum(II).

10. A compound claimed in claim 1, namely, (glycerato-O,O′)-cis-bis(methylamine)platinum(II).

11. A compound claimed in claim 1, namely, (2-ethylglycolato-O,O′)-cis-diammineplatinum(II).

12. A compound claimed in claim 1, namely, (2-isobutylglycolato-O,O′)-cis-diammineplatinum(II).

13. A compound claimed in claim 1, namely, (2-n-hexylglycolato-O,O′)-cis-diammineplatinum(II).

14. A pharmaceutical composition for treating transplanted malignant tumors comprising a pharmacologically effective amount of the compound claimed in claim 1 together with one or more carriers, diluents or excipients.

* * * * *